(12) United States Patent
Nie et al.

(10) Patent No.: US 11,759,228 B2
(45) Date of Patent: Sep. 19, 2023

(54) ULTRASONIC SURGICAL INSTRUMENT HAVING DETACHABLE SLEEVE ASSEMBLY

(71) Applicants: Ezisurg Medical Co., Ltd., Shanghai (CN); Ezisurg (Suzhou) Medical Co., Ltd., Jiangsu (CN)

(72) Inventors: Honglin Nie, Shanghai (CN); Zhidong Li, Shanghai (CN); Jidong Chen, Shanghai (CN); Wangtao Chang, Shanghai (CN)

(73) Assignees: EZISURG MEDICAL CO., LTD., Shanghai (CN); EZISURG (SUZHOU) MEDICAL CO., LTD., Jiangsu (CN)

( * ) Notice: Subject to any disclaimer, the term of this patent is extended or adjusted under 35 U.S.C. 154(b) by 175 days.

(21) Appl. No.: 16/957,955

(22) PCT Filed: Dec. 21, 2018

(86) PCT No.: PCT/CN2018/122781
§ 371 (c)(1),
(2) Date: Jun. 25, 2020

(87) PCT Pub. No.: WO2019/128876
PCT Pub. Date: Jul. 4, 2019

(65) Prior Publication Data
US 2020/0360046 A1   Nov. 19, 2020

(30) Foreign Application Priority Data

Dec. 25, 2017 (CN) .......................... 201711420747.2
Dec. 19, 2018 (CN) .......................... 201811557448.8

(51) Int. Cl.
*A61B 17/32* (2006.01)
*A61B 17/3211* (2006.01)
(Continued)

(52) U.S. Cl.
CPC .. *A61B 17/320092* (2013.01); *A61B 17/3211* (2013.01); *A61B 2017/0046* (2013.01);
(Continued)

(58) Field of Classification Search
CPC .... A61B 2017/0046; A61B 2017/2901; A61B 2017/00477; A61B 2017/2902;
(Continued)

(56) References Cited

U.S. PATENT DOCUMENTS

| 6,214,023 | B1 | 4/2001 | Whipple et al. |
| 2007/0084898 | A1* | 4/2007 | Scirica ............ A61B 17/07207 |
| | | | 227/176.1 |

(Continued)

FOREIGN PATENT DOCUMENTS

| CN | 107280735 A | 10/2017 |
| EP | 3656319 A1 | 5/2020 |
| WO | 2017100412 A1 | 6/2017 |

OTHER PUBLICATIONS

International Search Report and Written Opinion dated Feb. 27, 2019 in International Application PCT/CN2018/122781.

*Primary Examiner* — Kathleen S Holwerda
*Assistant Examiner* — Serenity A Miller
(74) *Attorney, Agent, or Firm* — Venable LLP

(57) ABSTRACT

The present application provides an ultrasonic surgical instrument with a detachable cannula component, comprising a cannula component and an instrument body, wherein the instrument body comprises a scalpel bar for realizing an ultrasonic cutting effect. The cannula component is mounted on the instrument body or dismounted from the instrument body along the longitudinal axis of the scalpel bar by a detachable structure. The present application also provides another ultrasonic surgical instrument with a detachable cannula component, comprising a detachable cannula com- (Continued)

ponent and an instrument body, wherein the instrument body comprises a non-detachable internal cannula and a scalpel bar capable of realizing an ultrasonic cutting effect. Compared with the prior art, the ultrasonic surgical instrument with a detachable cannula component of the present application has the advantages of being simple in structure, convenient to mount and dismount and low in use cost.

16 Claims, 12 Drawing Sheets

(51) Int. Cl.
 *A61B 17/00* (2006.01)
 *A61B 17/29* (2006.01)
(52) U.S. Cl.
 CPC ............... *A61B 2017/2901* (2013.01); *A61B 2017/320082* (2017.08); *A61B 2017/320093* (2017.08); *A61B 2017/320094* (2017.08)
(58) Field of Classification Search
 CPC ...... A61B 2017/291; A61B 2017/2946; A61B 2017/320093–320097; A61B 17/320092; A61B 17/320068
 See application file for complete search history.

(56) References Cited

U.S. PATENT DOCUMENTS

| | | |
|---|---|---|
| 2008/0021278 A1 | 1/2008 | Leonard et al. |
| 2012/0197190 A1* | 8/2012 | Suon ................. A61M 25/0147 604/95.04 |

* cited by examiner

ULTRASONIC SURGICAL INSTRUMENT HAVING DETACHABLE SLEEVE ASSEMBLY

CROSS REFERENCE TO RELATED APPLICATION

This application is a national stage application, filed under 35 U.S.C. § 371, of International Application PCT/CN2018/122781, filed on Dec. 21, 2018, entitled "ULTRASONIC SURGICAL INSTRUMENT HAVING DETACHABLE SLEEVE ASSEMBLY," which claims priority to Chinese Patent Application 201711420747.2 filed on Dec. 25, 2017 and Chinese Patent Application 201811557448.8 filed Dec. 19, 2018 which are incorporated herein by reference in their entireties.

TECHNICAL FIELD

The present application relates to a surgical instrument, and particularly relates to an ultrasonic surgical instrument with a detachable cannula component.

BACKGROUND

Along with popularization of minimally invasive surgery, ultrasonic scalpels have already become a kind of conventional surgical instrument. A scalpel blade of an ultrasonic scalpel performs mechanical oscillation with a certain ultrasonic frequency via an ultrasonic frequency generator, so that water molecules in tissues vaporize, protein hydrogen bonds rupture, and cells disrupt, and then tissues are cut off or coagulated, and blood vessels are closed. Ultrasonic scalpels realize tissue incision and blood coagulation at the same time and cause tiny lateral heat injury.

An ultrasonic scalpel is mainly composed of an ultrasonic frequency generator, a transducer and a surgical instrument. The ultrasonic frequency generator emits an oscillating electric signal, the transducer converts the oscillating electric signal into mechanical vibration, and the surgical instrument performs incision and blood coagulation on a tissue by utilizing the mechanical vibration of the transducer. A surgical instrument is generally formed by a scalpel bar, a pair of clamp forceps forming a clamping structure with a scalpel blade (a cutting portion at the head of the scalpel bar), a cannula encircling the outside of the scalpel bar, a grab handle and a grasping mechanism. The scalpel bar transmits the mechanical vibration of the transducer to the scalpel blade. The scalpel blade is matched with the clamp forceps to clamp a tissue to realize functions of incision and blood coagulation. The cannula isolates the scalpel bar from the outside to play a role of protecting and supporting the scalpel bar on one hand and forms a link mechanism with the clamp forceps to drive the clamp forceps to close and open on the other hand. The grab handle and the grasping mechanism are held by the hands of a doctor to operate the clamp forceps to open and close, and a switch is provided to control the ultrasonic frequency generator to start to output an oscillating electric signal or stop outputting an oscillating electric signal.

For mainstream ultrasonic scalpels on the market currently, a cannula of a surgical instrument is formed by an external cannula and an internal cannula, and a scalpel bar is located in the internal cannula. Clearances between the internal cannula and the external cannula and between the internal cannula and the scalpel bar are small. After one surgery is completed, blood or tissue fluid may enter the clearances between the internal cannula and the external cannula or between the internal cannula and the scalpel bar, and because the clearances are very small and narrow, it is difficult to thoroughly clean blood or tissue fluid entering the clearances. Therefore, the surgical instrument cannot be used repeatedly even if the structure and performances are still good, and may be only used as a disposable instrument, therefore, the use cost is very high.

In order to realize repeated use of the surgical instrument to lower the use cost, in some cases, a cannula, a scalpel bar and clamp forceps are designed to be a removable component structure, which can be used by only one time, while other parts can be repeatedly used for many times. Although such design lowers the cost to a certain extent, because cost of these parts including the cannula, the scalpel bar and the clamp forceps occupies a major portion of the cost of the surgical instrument, cost reduction effect is very limited. In some technical schemes, a cannula and clamp forceps are designed to be removable components, and can only be used by one time, while other parts, including a scalpel bar, all can be repeatedly used for many times, which can effectively lower the use cost. However, many parts are involved in the technical scheme, as a result, mounting and dismounting are inconvenient. There is also a technical scheme that an internal cannula is divided into a near end and a far end, the internal cannula and the external cannula as well as the clamp forceps at the far end can be dismounted and changed together, and other parts including the internal cannula and the scalpel bar can be repeatedly used. However, a connection structure of the internal cannula at the far end and a connection structure of the external cannula at the near end are complicated, and thus prove to be difficult to use in specific implementation(s).

SUMMARY

In order to solve the foregoing technical problem, the present application provides an ultrasonic surgical instrument with a detachable cannula component, which has the advantages of being simple in structure, convenient to mount and dismount and low in use cost in comparison with the prior art.

According to an aspect of the present application, an ultrasonic surgical instrument with a detachable cannula component is provided, including a cannula component and an instrument body, wherein the instrument body includes a scalpel bar realizing an ultrasonic cutting effect; the cannula component is mounted on the instrument body or dismounted from the instrument body by a detachable structure along the longitudinal axis of the scalpel bar.

Further, the detachable structure includes first detachable structures; the instrument body is fixedly connected with the cannula component by at least one of the first detachable structures.

Further, the first detachable structure includes a first boss, a first limiting slot, a stopper and an elastic element.

Optimally, the first limiting slot is a T-shaped limiting slot.

Further, the first boss is located on the cannula component, and the T-shaped limiting slot, the stopper and the elastic element are located on the instrument body. Alternatively, the first boss is located on the instrument body, and the T-shaped limiting slot, the stopper and the elastic element are located on the cannula component.

In a specific implementation mode, the T-shaped limiting slot includes a transverse slot parallel to a longitudinal axis of a scalpel bar and a vertical slot vertical to the longitudinal axis of the scalpel bar; the first boss is capable of sliding along the direction of the longitudinal axis of the scalpel bar in the transverse slot of the T-shaped limiting slot, and also being capable of sliding by being vertical to the direction of the longitudinal axis of the scalpel bar in the vertical slot of the T-shaped limiting slot; the stopper is configured to be capable of sliding along the direction of the longitudinal axis of the scalpel bar in the transverse slot of the T-shaped limiting slot, while incapable of entering the vertical slot of the T-shaped limiting slot; the stopper is connected with the elastic element, the elastic element is capable of providing an elastic force along the direction of the transverse slot of the T-shaped limiting slot, and the stopper is located at an intersected point of a transverse slot structure and a vertical slot structure of the T-shaped limiting slot in an initial state under the action of an elastic force of the elastic element.

In another specific implementation mode, the T-shaped limiting slot includes a transverse slot vertical to a longitudinal axis of a scalpel bar and a vertical slot parallel to the longitudinal axis of the scalpel bar; the first boss is capable of sliding along the direction of the longitudinal axis of the scalpel bar in the vertical slot of the T-shaped limiting slot, and also is capable of sliding by being vertical to the direction of the longitudinal axis of the scalpel bar in the transverse slot of the T-shaped limiting slot; the stopper is configured to be capable of sliding by being vertical to the direction of the longitudinal axis of the scalpel bar in the transverse slot of the T-shaped limiting slot, while incapable of entering the vertical slot of the T-shaped limiting slot; the stopper is connected with the elastic element, the elastic element is capable of providing an elastic force along the direction of the transverse slot of the T-shaped limiting slot, and the stopper is located at an intersected point of a transverse slot structure and a vertical slot structure of the T-shaped limiting slot in an initial state under the action of an elastic force of the elastic element.

Optimally, the first boss is an excircle boss or an inner circle boss.

According to a second aspect of the present application, an ultrasonic surgical instrument with a detachable cannula component is provided, including a cannula component and an instrument body, wherein the instrument body includes a scalpel bar realizing an ultrasonic cutting effect; the cannula component is mounted on the instrument body or dismounted from the instrument body by the detachable structure along the longitudinal axis of the scalpel bar.

Further, the cannula component includes an internal cannula, an external cannula and a pair of clamp forceps located at a far end; the external cannula and the internal cannula are both provided by being coaxial with the scalpel bar; the clamp forceps are rotatably connected with the external cannula by a first rotating shaft and are rotatably connected with the internal cannula by a second rotating shaft, so that the internal cannula is pulled forwards and backwards along an axial direction to drive the clamp forceps to rotate around the first rotating shaft.

In an implementation mode, the detachable structure includes a first detachable structure and a second detachable structure; the instrument body is fixedly connected with the cannula component by the first detachable structure, and the instrument body is in drive connection with the cannula component by the second detachable structure.

Optimally, the instrument body is fixedly connected with the external cannula by the first detachable structure, and the instrument body is in drive connection with the internal cannula by the second detachable structure.

Further, the first detachable structure includes a first boss located on the external cannula, and a first limiting slot, a stopper and an elastic element located on the instrument body.

Optimally, the first limiting slot is a T-shaped limiting slot.

Optimally, the cannula component also includes an external cannula fastener and an internal cannula fastener; the external cannula fastener is fixedly connected with the external cannula, the internal cannula fixing fastener is fixedly connected with the internal cannula; and the first boss is provided on the external cannula fastener.

In a specific implementation mode, the T-shaped limiting slot includes a transverse slot parallel to a longitudinal axis of a scalpel bar and a vertical slot vertical to the longitudinal axis of the scalpel bar; the first boss is capable of sliding along the direction of the longitudinal axis of the scalpel bar in the transverse slot of the T-shaped limiting slot, and also is capable of sliding by being vertical to the direction of the longitudinal axis of the scalpel bar in the vertical slot of the T-shaped limiting slot; the stopper is configured to be capable of sliding along the direction of the longitudinal axis of the scalpel bar in the transverse slot of the T-shaped limiting slot, while incapable of entering the vertical slot of the T-shaped limiting slot; the stopper is connected with the elastic element, the elastic element is capable of providing an elastic force along the direction of the transverse slot of the T-shaped limiting slot, and the stopper is located at an intersected point of a transverse slot structure and a vertical slot structure of the T-shaped limiting slot in an initial state under the action of an elastic force of the elastic element.

In another specific implementation mode, the T-shaped limiting slot includes a transverse slot vertical to a longitudinal axis of a scalpel bar and a vertical slot parallel to the longitudinal axis of the scalpel bar; the first boss is capable of sliding along the direction of the longitudinal axis of the scalpel bar in the vertical slot of the T-shaped limiting slot, and also is capable of sliding by being vertical to the direction of the longitudinal axis of the scalpel bar in the transverse slot of the T-shaped limiting slot; the stopper is configured to be capable of sliding by being vertical to the direction of the longitudinal axis of the scalpel bar in the transverse slot of the T-shaped limiting slot, while incapable of entering the vertical slot of the T-shaped limiting slot; the stopper is connected with the elastic element, the elastic element is capable of providing an elastic force along the direction of the transverse slot of the T-shaped limiting slot, and the stopper is located at an intersected point of a transverse slot structure and a vertical slot structure of the T-shaped limiting slot in an initial state under the action of an elastic force of the elastic element.

Further, a fixed seat is provided on the instrument body, and the T-shaped limiting slot is provided on the fixed seat.

Further, a thumbwheel and an elastic element are mounted on the fixed seat, the stopper is provided on the thumbwheel, the thumbwheel is capable of driving the stopper to move along the direction of the transverse slot of the T-shaped limiting slot by overcoming the elastic force of the elastic element so that the stopper opens an intersection of the transverse slot and the vertical slot of the T-shaped limiting slot.

Further, the thumbwheel drives the stopper to move along the direction of the transverse slot of the T-shaped limiting slot by overcoming the elastic force of the elastic element so that the stopper opens an intersection of the transverse slot and the vertical slot of the T-shaped limiting slot to cause the first boss to slide into the vertical slot from the transverse slot of the T-shaped limiting slot or slide into the transverse slot from the vertical slot, and then the thumbwheel drives the stopper to move along the direction of the transverse slot of the T-shaped limiting slot under the action of the elastic force of the elastic element so that the stopper is located at an intersection of the transverse slot and the vertical slot of the T-shaped limiting slot to cause first boss to be incapable of sliding out from the vertical slot or the transverse slot, thereby realizing fixed connection between the instrument body and the external cannula.

Further, the first boss is an excircle boss or an inner circle boss.

In an implementation mode, the second detachable structure includes a second limiting slot located on the cannula component and a second boss located on the instrument body.

Optimally, the second limiting slot is an L-shaped limiting slot.

Optimally, the L-shaped limiting slot is located on the internal cannula.

Further, the transverse slot of the L-shaped limiting slot is along the axis direction of the scalpel bar, the vertical slot of the L-shaped limiting slot is vertical to the direction of the longitudinal axis of the scalpel bar; the second boss is capable of sliding along the direction of the longitudinal axis of the scalpel bar in the transverse slot of the L-shaped limiting slot and sliding by being vertical to the direction of the longitudinal axis of the scalpel bar in the vertical slot of the L-shaped limiting slot.

Alternatively, the vertical slot of the L-shaped limiting slot is along the direction of the longitudinal axis of the scalpel bar, the transverse slot of the L-shaped limiting slot is vertical to the direction of the longitudinal axis of the scalpel bar; the second boss is capable of sliding along the direction of the longitudinal axis of the scalpel bar in the vertical slot of the L-shaped limiting slot and sliding by being vertical to the direction of the longitudinal axis of the scalpel bar in the transverse slot of the L-shaped limiting slot.

Optimally, a driving seat is connected to the instrument body, the second boss is provided on the driving seat; and the driving seat and the second boss can be driven to move forwards and backwards along the axis direction of the scalpel bar by a manual control mechanism on the instrument body.

Further, the second detachable structure moves along with the movement of the first detachable structure in the process of mounting or dismounting the cannula component and the instrument body.

Specifically, when the first boss on the first detachable structure is about to enter the T-shaped limiting slot, the second boss on the second detachable structure also is about to enter the L-shaped limiting slot; when the first boss on the first detachable structure enters an intersected point of the transverse slot and the vertical slot of the T-shaped limiting slot, the second boss on the second detachable structure also enters an intersected point of the transverse slot and the vertical slot of the L-shaped limiting slot; when the external cannula is rotated to cause the first boss on the first detachable structure to completely enter the vertical slot from the transverse slot of the T-shaped limiting slot or enter the transverse slot from the vertical slot, the internal cannula rotates therewith, so that the second boss on the second detachable structure also completely enters the vertical slot from the transverse slot of the L-shaped limiting slot or enters the transverse slot from the vertical slot.

Further, the second boss is an excircle boss or an inner circle boss.

Optimally, the first detachable structure and the second detachable structure are interchangeable, that is, the first detachable structure includes a second boss and the L-shaped limiting slot.

Optimally, positions of the first boss and the T-shaped limiting slot are interchanged.

Optimally, positions of the second boss and the L-shaped limiting slot are interchanged.

According to a third aspect of the present application, an ultrasonic surgical instrument with a detachable cannula component is provided, including a detachable cannula component and an instrument body, wherein the instrument body includes a non-detachable internal cannula and a scalpel bar capable of realizing an ultrasonic cutting effect; and the detachable cannula component can be mounted on or dismounted from the instrument body along the axis of the scalpel bar.

Further, the detachable cannula component includes an external cannula, a detachable internal cannula, and a pair of clamp forceps located at a far end; the external cannula and the detachable internal cannula are both provided by being coaxial with the scalpel bar; the clamp forceps are rotatably connected with the external cannula by a first rotating shaft and are rotatably connected with the detachable internal cannula by a second rotating shaft, so that the detachable internal cannula is pulled forwards and backwards along an axial direction to drive the clamp forceps to rotate around the first rotating shaft.

In an implementation mode, the detachable structure includes a first detachable structure and a second detachable structure; the instrument body is fixedly connected with the detachable cannula component by the first detachable structure, and the instrument body is in drive connection with the detachable cannula component by the second detachable structure.

Further, the detachable internal cannula is located at a far end of the detachable cannula component, and the external cannula extends to a far end from a near end of the detachable cannula component.

Further, the first detachable structure includes a first boss, a first limiting slot, a stopper and an elastic element.

Further, a non-detachable internal cannula of the instrument body is in drive connection with a detachable internal cannula of the cannula component by the second detachable structure.

Further, the second detachable structure includes a second limiting slot located on the detachable cannula component and a second boss located on the instrument body.

Optimally, the second limiting slot is an L-shaped limiting slot.

Specifically, the L-shaped limiting slot is located on the detachable internal cannula, and the second boss is located on the non-detachable internal cannula of the instrument body.

Further, the non-detachable internal cannula is sealed with the scalpel bar by a far-end sealing ring; and the non-detachable internal cannula is sealed with the detachable cannula component by a near-end sealing ring.

Further, the far-end sealing ring is a silica gel ring.

Further, a shaft shoulder is provided on one of sealed joints of the far-end sealing ring and the scalpel bar, a full-circle groove structure is provided on the other one, and the shaft shoulder is in tight fit with the full-circle groove structure.

In an implementation mode, an internal cannula fastener is provided at the near end of the non-detachable internal cannula, and the near-end sealing ring is mounted in the groove of the internal cannula fastener, and located between the internal cannula fastener and the external cannula fastener.

The first detachable structure and the second detachable structure are similar to the foregoing descriptions about the first aspect and the second aspect of the present application.

The process of mounting or dismounting the detachable cannula component and the instrument body are basically similar to the foregoing descriptions about the first aspect and the second aspect of the present application, and under the effects of stop and push of the first detachable structure, the second detachable structure moves along with the movement of the first detachable structure in the process of mounting or dismounting the detachable cannula component and the instrument body; specifically, when the first boss on the first detachable structure is about to enter the first limiting slot, the second boss on the second detachable structure also is about to enter the L-shaped limiting slot; when the first boss on the first detachable structure enters an intersected point of the transverse slot and the vertical slot of the T-shaped limiting slot, the second boss on the second detachable structure also enters an intersected point of the transverse slot and the vertical slot of the L-shaped limiting slot; when the external cannula fastener is rotated to cause the first boss on the first detachable structure to enter the vertical slot from the transverse slot of the T-shaped limiting slot or enter the transverse slot from the vertical slot, the detachable internal cannula rotates therewith, so that the second boss on the second detachable structure also completely enters the vertical slot from the transverse slot of the L-shaped limiting slot or enters the transverse slot from the vertical slot. At the moment, the non-detachable internal cannula and the detachable internal cannula complete drive connection, to realize drive control of the instrument body on the cannula component. When the detachable cannula component is dismounted from the instrument body, it is a reverse process of the foregoing process, and is not further described herein.

Further, the second boss is an excircle boss or an inner circle boss.

Optimally, the first detachable structure and the second detachable structure are interchangeable, that is, the first detachable structure includes a second boss and the L-shaped limiting slot.

Optimally, positions of the first boss and the T-shaped limiting slot are interchanged.

Optimally, positions of the second boss and the L-shaped limiting slot are interchanged.

According to the reusable ultrasonic surgical instrument of the present application, the cannula component is detachably connected with the instrument body, and is conveniently dismounted after use to be cleaned, and then can be used repeatedly, thereby solving the problem that mainstream ultrasonic surgical instruments on the market are difficult to clean after being used and cannot be used repeatedly, and remarkably lowering the use cost of the instrument. Moreover, in comparison with other implementation schemes, the reusable ultrasonic surgical instrument disclosed by the present application has the advantages of being simple in structure, convenient to mount and dismount and low in use cost.

DESCRIPTION OF THE EMBODIMENTS

The following clearly and completely describes the technical schemes in the embodiments of the present application, apparently, the described embodiments are merely some of the embodiments of the present application rather than all of the embodiments. All other embodiments obtained by a person of ordinary skill in the art based on the embodiments of the present application without creative efforts shall fall within the protection scope of the present disclosure.

For the convenience of description, "near end" in the whole application refers to an end close to an operator after the operator holds an instrument, and "far end" refers to an end far away from the operator after the operator holds the instrument.

FIGS. 1-13 describe an ultrasonic surgical instrument with a detachable cannula according to a first embodiment of the present application.

Figure 1:
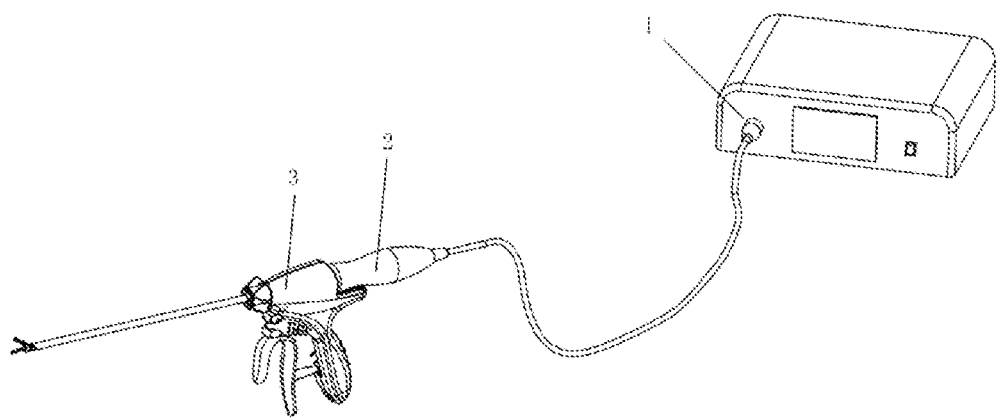
FIG. 1 is a schematic diagram of an ultrasonic surgical system with a detachable cannula.

Referring to FIG. 1, an ultrasonic surgical system with a detachable cannula according to the present disclosure is shown, including an ultrasonic frequency generator 1, a transducer 2 and a surgical instrument 3. The ultrasonic frequency generator 1 emits an oscillating electric signal and transmits to the transducer 2, the transducer 2 converts the oscillating electric signal into mechanical vibrations and transmits the vibrations to the surgical instrument 3. The surgical instrument 3 performs incision or blood coagulation on a tissue by utilizing the mechanical vibrations of the transducer 2.

Figure 2:
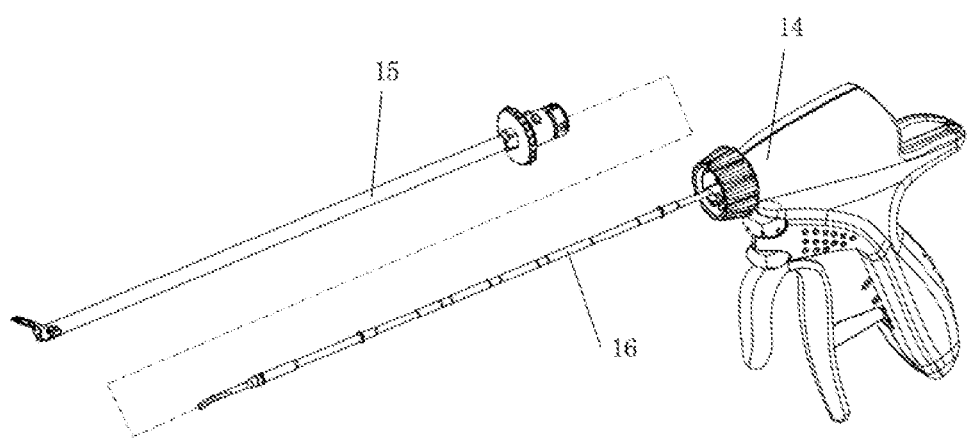
FIG. 2 is a schematic diagram of an ultrasonic surgical instrument according to a first embodiment of the present application, wherein the cannula component has already been dismounted from the instrument body.

Referring to FIG. 1 and FIG. 2, the surgical instrument 3 includes an instrument body 14 and a cannula component 15. The instrument body 14 includes a scalpel bar 16 transmitting mechanism vibration of the transducer 2 to a scalpel blade (a cutting portion at the head of the scalpel bar); the cannula component 15 can be mounted on the instrument body 14 or dismounted from the instrument body 14 along the axis of the scalpel bar 16. The cannula component 15 in FIG. 2 has already been dismounted from the instrument body 14.

Figure 3:
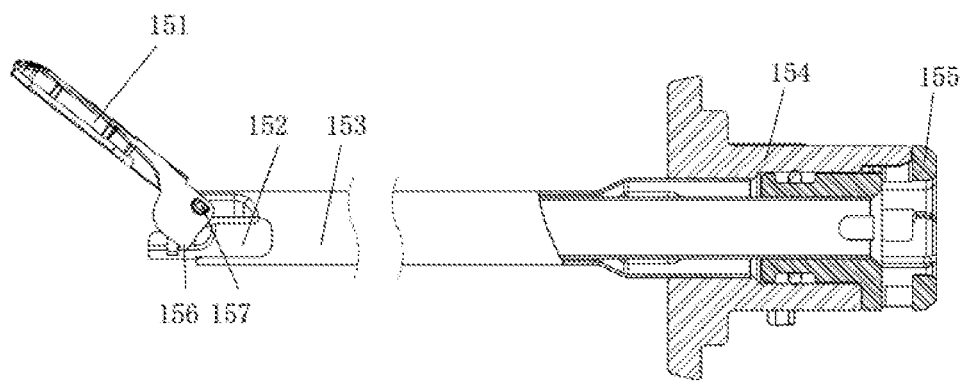
FIG. 3 is a schematic structure diagram of a cannula component in FIG. 2.

FIG. 3 shows a detailed structure of a cannula component 15 according to the present application, and the cannula component 15 includes a pair of clamp forceps 151 located at a far end and forming a clamping structure with a scalpel blade, an internal cannula 152, an external cannula 153, an external cannula fastener 154 and an internal cannula fastener 155. The internal cannula 152 and the external cannula 153 are both provided by being coaxial with the scalpel bar 16. The external cannula fastener 154 is fixedly connected with the external cannula 153, the internal cannula fastener 155 is fixedly connected with the internal cannula 152, and modes such as co-injection, gluing, welding or interference fitting or other modes familiar to a person of ordinary skill in the art may be selected as a fixed connection mode according to different part materials. The clamp forceps 151 are rotatably connected with the external cannula 153 by a first rotating shaft 157 and are rotatably connected with the internal cannula 152 by a second rotating shaft 156. Therefore, after the external cannula fastener 154 is fixed, the internal cannula fastener 155 is pulled forwards and backwards along an axial direction to drive the clamp forceps 151 to rotate around a rotating shaft 157, so as to realize operation on the actions of opening or closing of the clamp forceps 151 relative to the scalpel blade of the scalpel bar 16 via the instrument body 14 after the cannula component 15 is assembled to the instrument body 14. The scalpel blade is matched with the clamp forceps 151 to clamp a tissue and perform ultrasonic cutting and hemostasis on the clamped tissue; the cannula component 15 isolates the scalpel bar 16 from the outside to play a role of protecting the scalpel bar.

Figure 4:
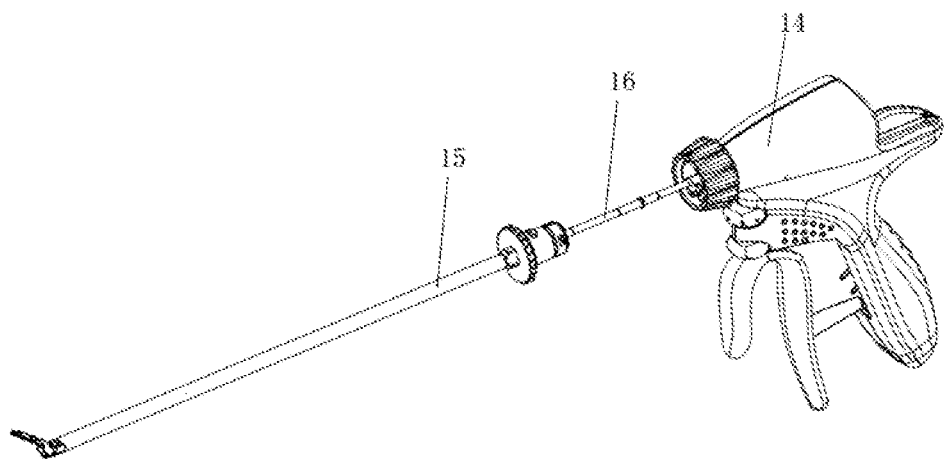
FIG. 4 is a schematic connection diagram of the cannula component and the instrument body in FIG. 2, wherein the cannula component is not completely mounted into the instrument body.

FIG. 4 is a schematic connection diagram of the cannula component and the instrument body, wherein the cannula component 15 is not completely mounted into the instrument body 14; it needs to penetrate a scalpel bar 16 on the instrument body 14 into the cannula component 15 until a scalpel blade penetrates out.

According to an implementation mode of the present application, a function of mounting or dismounting between the cannula component 15 and the instrument body 14 is realized by a first detachable structure 31 and a second detachable structure 32. The first detachable structure 31 is as shown in FIG. 5 to FIG. 8, and the first detachable structure 31 is a fixed connection structure between the instrument body 14 and the cannula component 14, and can fixedly connect the instrument body 14 with the cannula component 15; the second detachable structure 32 is as shown in FIG. 9 to FIG. 12, and the second detachable structure 32 is a drive connection structure of the instrument body 14 and the cannula component 15, and can realize drive control of the instrument body 14 on the clamp forceps 151 of the cannula component 15. The second detachable structure 32 is provided by being coaxial with the first detachable structure 31 and can implement finite movement relative to the first detachable structure 31 along the axial direction of the scalpel bar 16.

Referring to FIGS. 5-8, in the ultrasonic surgical instrument with a detachable cannula according to the first embodiment of the present application, the first detachable structure 31 includes a first boss 312 located at a near end of the cannula component 15, and a T-shaped limiting slot 311, a stopper 313 (i.e., a stopping element) and an elastic element 314 located on the instrument body 14. A person skilled in the art may easily think that positions of the first boss and the T-shaped limiting slot 311 and positions of the stopper 313 and the elastic element 314 are interchangeable, that is, the first boss is provided on the instrument body 14, while the T-shaped limiting slot 311, the stopper 313 and the elastic element 314 are provided on the cannula component 15.

More precisely, a fixed seat 3110 is provided on a shell 141 of the instrument body 14, the T-shaped limiting slot 311 is provided on the fixed seat 3110 and includes a transverse slot 3111 parallel to the longitudinal axis of a scalpel bar and a vertical slot 3112 vertical to the longitudinal axis of the scalpel bar. The first boss 312 is provided on external cannula fastener 154. The first boss 312 is capable of sliding along the axis direction of the scalpel bar in the transverse slot 3111 of the T-shaped limiting slot, the first boss 312 also is capable of sliding by being vertical (i.e., a vertical orientation) to the axis direction of the scalpel bar in the vertical slot 3112 of the T-shaped limiting slot. The stopper 313 is capable of sliding along the axis direction of the scalpel bar in the transverse slot 3111 of the T-shaped limiting slot, while incapable of entering the vertical slot 3112 of the T-shaped limiting slot. The stopper 313 is connected with the elastic element 314. The elastic element 314 is capable of providing an elastic force along the direction of the transverse slot 3111 of the T-shaped limiting slot, and the stopper is located at an intersected point of a transverse slot structure and a vertical slot structure of the T-shaped limiting slot in an initial state under the action of an elastic force of the elastic element 314.

Figure 5:
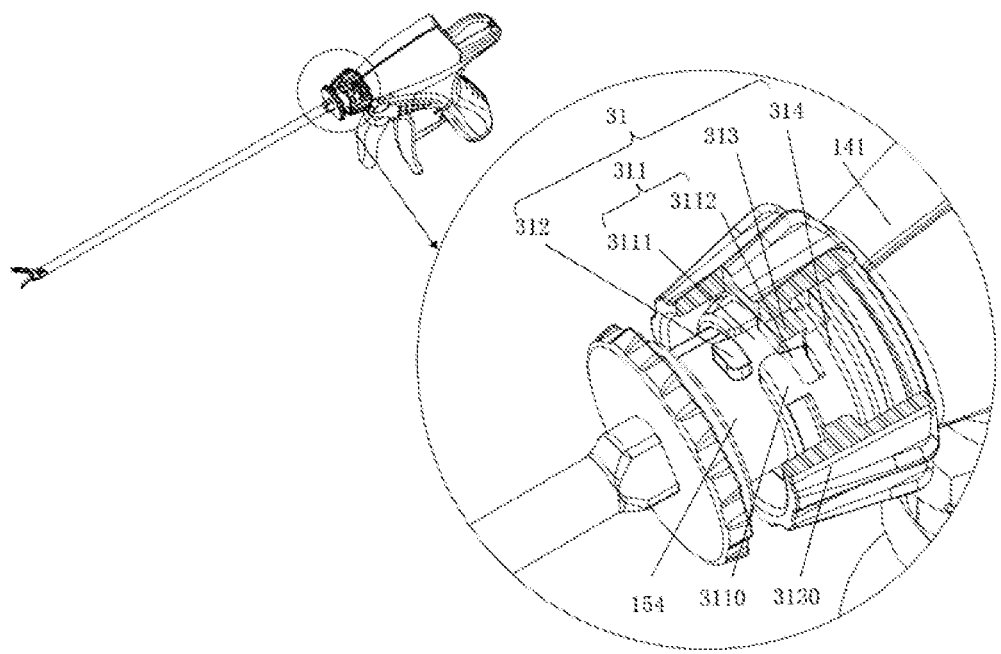
FIG. 5 is a schematic diagram of a first detachable structure in FIG. 2, wherein the first boss is about to enter the T-shaped limiting slot.

Referring to FIG. 5, a fixed seat 3110 is provided on a shell 141 of the instrument body 14, a thumbwheel 3130 and the elastic element 314 are mounted on the fixed seat 3110, the T-shaped limiting slot 311 is provided on the fixed seat 3110, and the stopper 313 is provided on the thumbwheel 3130.

Figure 6:
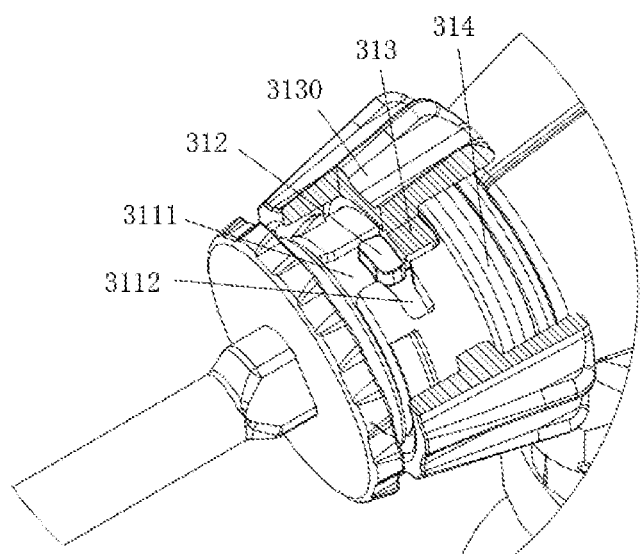
FIG. 6 is a schematic diagram of a first detachable structure in FIG. 2, wherein the first boss enters an intersection of the transverse slot and the vertical slot of the T-shaped limiting slot.
Figure 7:
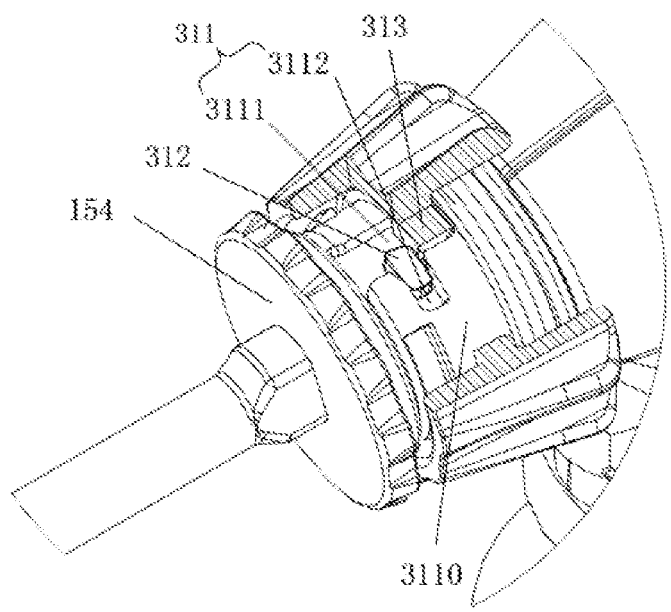
FIG. 7 is a schematic diagram of a first detachable structure in FIG. 2, wherein the first boss enters a half position of the vertical slot of the T-shaped limiting slot.
Figure 8:
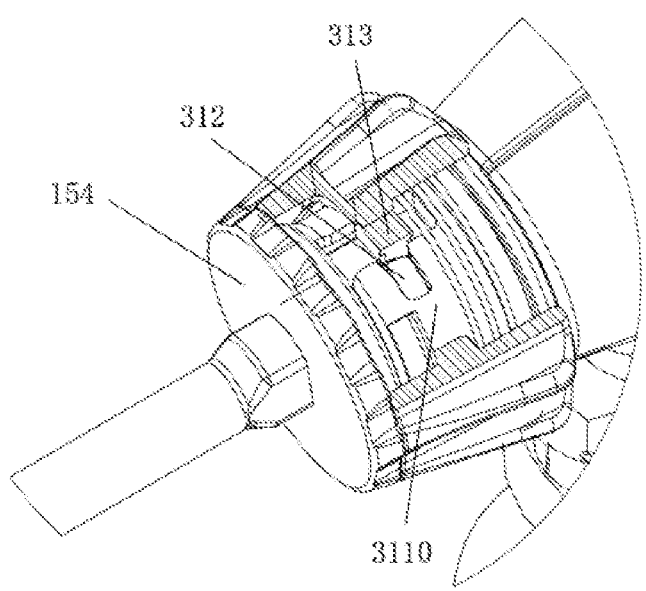
FIG. 8 is a schematic diagram of a first detachable structure in FIG. 2, wherein the first boss enters the vertical slot of the T-shaped limiting slot and is blocked by the stopper.

Referring to FIG. 5 to FIG. 8, wherein FIG. 5 shows that the first boss 312 is about to enter the T-shaped limiting slot 311. In an initial state, the stopper 313 is located at an intersected point of a transverse slot 3111 and a vertical slot 3112 of the T-shaped limiting slot and seals an outlet of the vertical slot 3112 under the action of an elastic force of the elastic element 314. When the first boss 312 continues to slide towards the inside of the transverse slot 3111 of the T-shaped limiting slot 311 under the action of an external force, the stopper 313 needs to be pushed to slide in the transverse slot 3111 by overcoming the elastic force of the elastic element 314. FIG. 6 shows a situation when the first boss 312 enters an intersection of the transverse slot 3111 and the vertical slot 3112, at the moment, the external cannula fastener 154 is rotated to drive the first boss 312 to slide into the vertical slot 3112 of the T-shaped limiting slot, FIG. 7 shows such state. Continue to rotate the external cannula fastener 154, to cause the first boss 312 to completely slide into the vertical slot 3112, and the stopper 313 returns to the intersection of the transverse slot 3111 and the vertical slot 3112 under the action of the elastic element 314, so as to seal an outlet of the vertical slot 3112 to completely confine the first boss 312 in the vertical slot 3112, FIG. 8 describes such state, at the moment, the external cannula fastener 154 is fixed on the fixed seat 3110, and fixed connection between the cannula component 15 and the instrument body 14 is completed by the first detachable structure 31.

When the cannula component 15 is dismounted from the instrument body 14, it is basically a reverse operation of the process described in FIG. 5 to FIG. 8. Firstly, the thumbwheel 3130 is pulled towards a near end along the axis direction of the scalpel bar by overcoming the elastic force of the elastic element 314, so that the stopper 313 opens an intersection of the transverse slot 3111 and the vertical slot 3113 of the T-shaped limiting slot 311, then the external cannula fastener 154 is rotated to cause the first boss 312 to slide into the transverse slot 3111 from the vertical slot 3112 of the T-shaped limiting slot 311, and then the cannula component 15 is pulled out from the instrument body 14 along the axis direction of the scalpel bar to cause the first boss 312 to slide out of the transverse slot 3111, thus completing the dismounting process. In such process, along with the movement of the first boss 312 towards a far side along the transverse slot from the intersection of the transverse slot 3111 and the vertical slot 3112, the stopper 313 returns to the intersection of the transverse slot 3111 and the vertical slot 3112 under the action of elastic force of the elastic element 314.

A person of ordinary skill in the art may understand that multiple first detachable structures 31 may be provided on the near end of the cannula component 15 and the instrument body 14, optimally, the multiple first detachable structures 31 are symmetrically provided by taking the scalpel bar 16 as an axis, and specific implementation modes thereof all fall within the protection scope of the present application.

Refer to FIG. 9-12, in the ultrasonic surgical instrument with a detachable cannula according to the first embodiment of the present application, a second detachable structure 32 includes an L-shaped limiting slot 321 located on an internal cannula fastener 155 and a second boss 322 on the instrument body 14. A person skilled in the art may easy think that positions of the second boss and the L-shaped limiting slots are interchangeable. Specifically, a driving seat 3220 is connected to the instrument body 14, the second boss 322 is provided on the driving seat 3220; the driving seat 3220 and the second boss 322 can be driven to move forwards and backwards along the axis direction of the scalpel bar 16 by a manual control mechanism on the instrument body 14.

Figure 10:
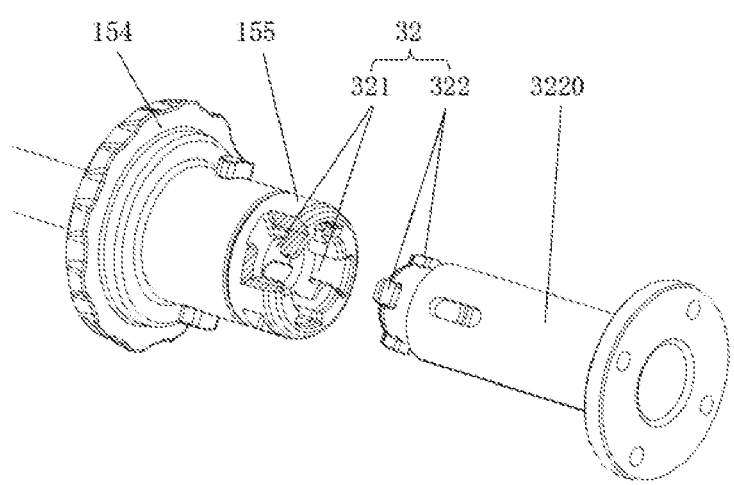
FIG. 10 is a schematic diagram of a second detachable structure in FIG. 2, in which schematic structure diagrams of the second boss and the L-shaped limiting slot are shown.

FIG. 10 shows a detailed schematic structure diagram of L-shaped limiting slots 321 and second bosses 322, it is known from FIG. 10 that multiple L-shaped limiting slot structures 321 are provided on the internal cannula fastener 155, and multiple second bosses 322 are provided on the driving seat 3220.

Figure 9:
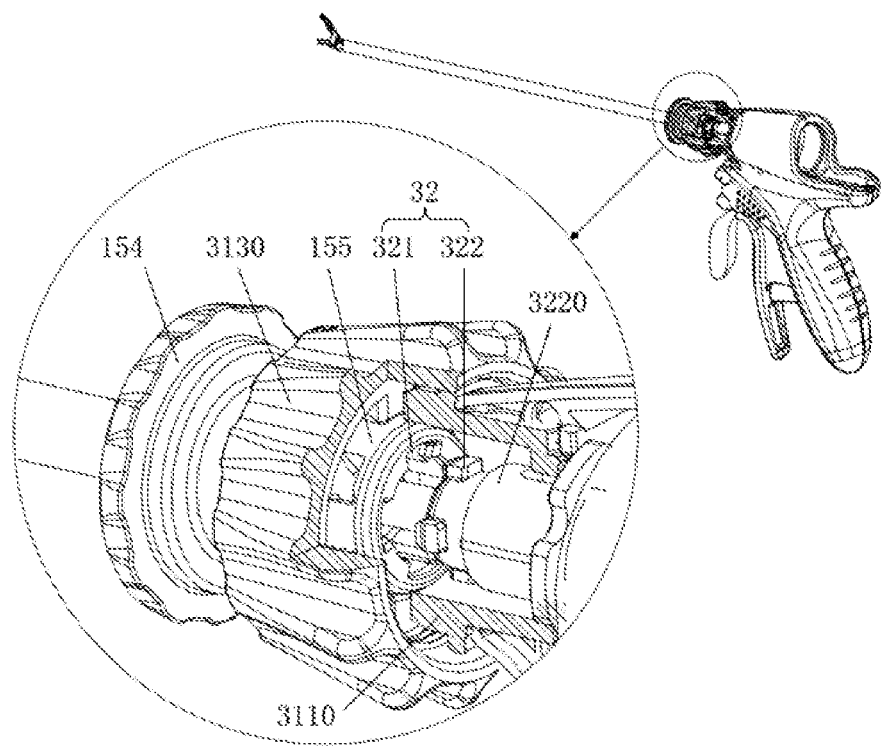
FIG. 9 is a schematic diagram of a second detachable structure in FIG. 2, wherein the second boss is about to enter the L-shaped limiting slot.
Figure 11:
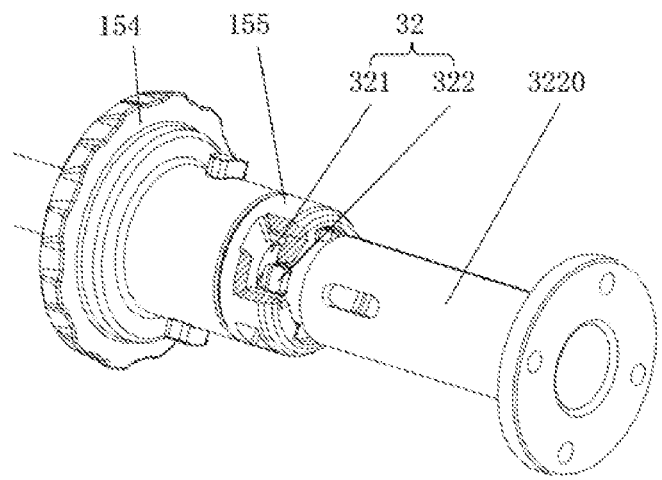
FIG. 11 is a schematic diagram of a second detachable structure in FIG. 2, wherein the second boss enters the transverse slot of the L-shaped limiting slot.
Figure 12:
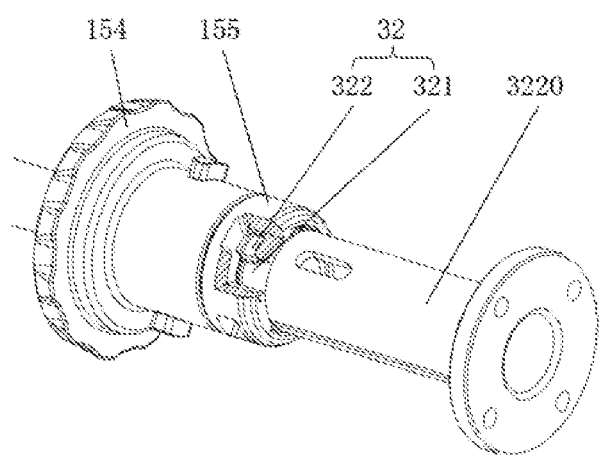
FIG. 12 is a schematic diagram of a second detachable structure in FIG. 2, wherein the second boss enters the vertical slot of the L-shaped limiting slot.

FIGS. 9, 11, 12 show a mounting process of the second detachable structure 32, and under the effects of stop and push of the first detachable structure 31, the second detachable structure 32 moves along with the movement of the first detachable structure 31 in the process of mounting or dismounting the cannula component 15 and the instrument body 14. Specifically, as shown in FIG. 9, when the first boss 312 on the first detachable structure 31 is about to enter the T-shaped limiting slot 311, the second boss 322 on the second detachable structure 32 also is about to enter the L-shaped limiting slot 321. As shown in FIG. 11, when the first boss 312 on the first detachable structure 31 completely enters the transverse slot 3111 of the T-shaped limiting slot 311, the second boss 322 on the second detachable structure 32 also completely enters the transverse slot of the L-shaped limiting slot 321. As shown in FIG. 12, when the external cannula fastener 154 is rotated to cause the first boss 312 on the first detachable structure 31 to completely enter the vertical slot 3112 of the T-shaped limiting slot 311, the internal cannula fastener 155 rotates therewith, so that the second boss 322 on the second detachable structure 32 also completely enters the vertical slot of the L-shaped limiting slot 321. At the moment, drive connection between the internal cannula fastener 155 and the driving seat 3220 is completed, to realize drive control of the instrument body 14 on the cannula component 15. When the cannula component 15 is dismounted from the instrument body 14, it is a reverse process of the foregoing process, and is not further described herein.

A person of ordinary skill in the art may understand that one or multiple second detachable structures 32 may be provided, optimally, as shown in FIG. 10, the multiple second detachable structures 32 are symmetrically arranged by taking the scalpel bar 16 as an axis, and specific implementation modes all fall within a protection scope of the present application.

Figure 13:
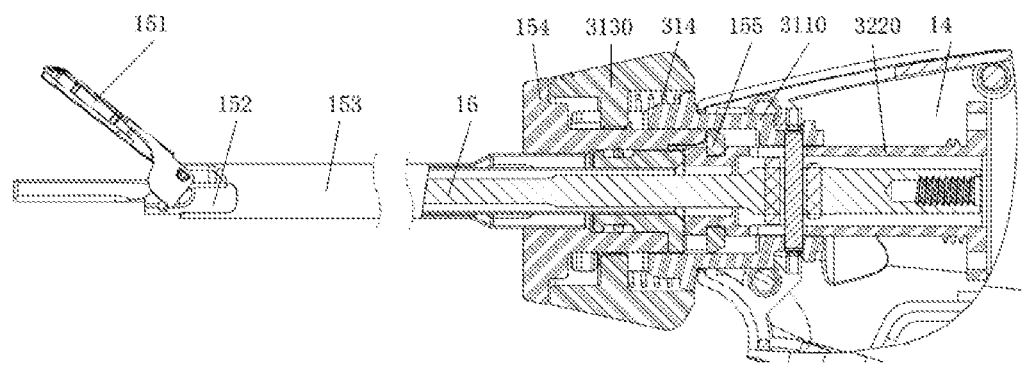
FIG. 13 is a structure profile diagram after the cannula component and the instrument body of the ultrasonic surgical instrument in FIG. 2 are mounted.

FIG. 13 shows a structure profile diagram after the cannula component 15 and the instrument body 14 are mounted, and structure details of connection of the external cannula fastener 154 with a fixed seat 3110 by a first detachable structure 31 and connection of the internal cannula fastener 155 with a driving seat 3220 by a second detachable structure 32 can be more clearly seen in more details from FIG. 13.

FIGS. 14-24 describe an ultrasonic surgical instrument with a detachable cannula according to a second embodiment of the present application.

An overall structure of an ultrasonic surgical system with a detachable cannula of the present embodiment is similar to that of the system of the first embodiment, as shown in FIG. 1, including an ultrasonic frequency generator 1, a transducer 2 and a surgical instrument 3. The ultrasonic frequency generator 1 emits an oscillating electric signal and transmits to the transducer 2, the transducer 2 converts the oscillating electric signal into mechanical vibration and transmits to the surgical instrument 3, and the surgical instrument 3 performs incision or blood coagulation on a tissue by utilizing the mechanical vibration of the transducer 2.

Figure 14:
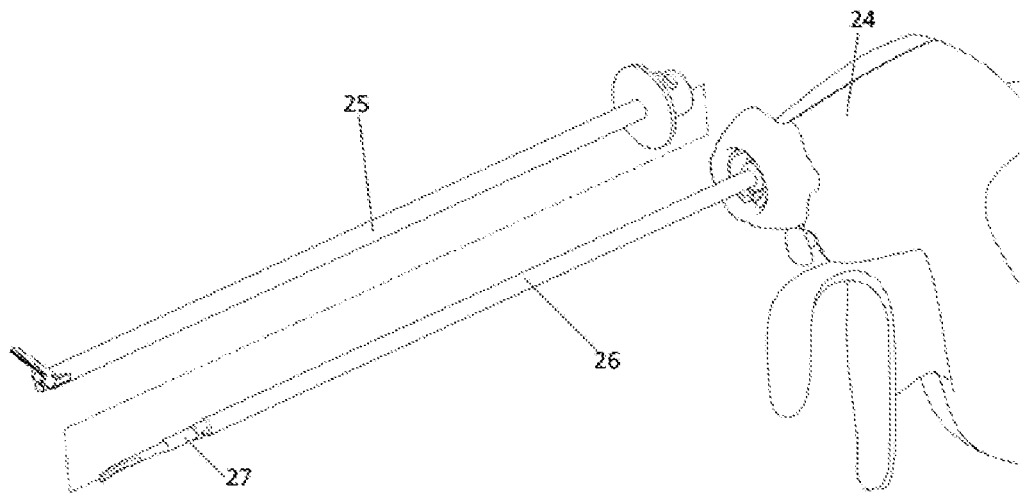
FIG. 14 is a schematic diagram of an ultrasonic surgical instrument according to a second embodiment of the present application, wherein the cannula component has already been dismounted from the instrument body.

Referring to FIG. 14, the surgical instrument 3 includes an instrument body 24 and a detachable cannula component 25. The instrument body 24 includes a non-detachable internal cannula 26 and a scalpel bar 27 capable of realizing an ultrasonic cutting effect; the cannula component 25 can be mounted on the instrument body 24 or dismounted from the instrument body 24 along the axis of the scalpel bar 27.

Figure 15:
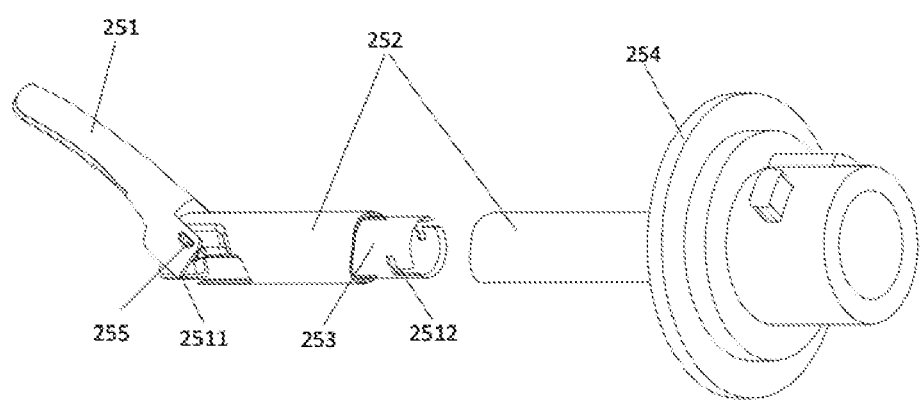
FIG. 15 is a schematic structure diagram of a cannula component in FIG. 14.

FIG. 15 shows a detailed structure of the cannula component 25, and a far end of the cannula component 25 includes a pair of clamp forceps 251 forming a clamping structure with a scalpel blade, a detachable internal cannula 253 and a first rotating shaft 255. A near end of the cannula component 25 includes an external cannula fastener 254, and also includes an external cannula 252 extending from a near end to a far end. The external cannula 252 and the detachable internal cannula 253 are both provided by being coaxial with the scalpel bar 27. The external cannula fastener 254 is fixedly connected with the external cannula 252, and modes such as co-injection, gluing, welding or interference fitting or other modes familiar to a person of ordinary skill in the art may be selected as a fixed connection mode according to different part materials. The clamp forceps 251 are rotatably connected with the external cannula 252 by a first rotating shaft 255 and are rotatably connected with the detachable internal cannula 253 by a second rotating shaft 2511. Therefore, after the external cannula fastener 254 is fixed, the detachable internal cannula 253 is pulled forwards and backwards along an axial direction to drive the clamp forceps 251 to rotate around the first rotating shaft 255, so as to realize operation on the actions of opening or closing of the clamp forceps 251 relative to the scalpel blade of the scalpel bar 27 via the instrument body 24 after the cannula component 25 is assembled to the instrument body 24. The scalpel blade of the scalpel bar 27 is matched with the clamp forceps 251 to clamp a tissue and perform ultrasonic cutting and hemostasis on the clamped tissue; the detachable cannula component 25 isolates the scalpel bar 27 from the outside to play a role of protecting the scalpel bar 27.

Figure 16:
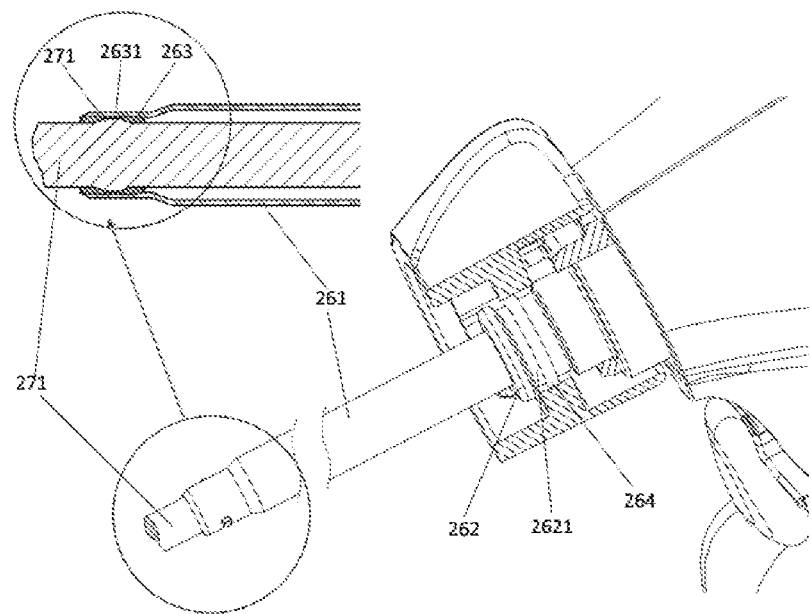
FIG. 16 is a sealed structure diagram of a non-detachable internal cannula in FIG. 14.

FIG. 16 shows sealed structure diagrams between a non-detachable internal cannula 26 and a scalpel bar 27 and between a non-detachable internal cannula 26 and a detachable cannula component 25. The non-detachable internal cannula 26 includes an internal cannula 261 and an internal cannula fastener 262 which are fixedly connected together. Modes such as co-injection, gluing, welding or interference fitting or other modes familiar to a person of ordinary skill in the art may be selected as a fixed connection mode according to different part materials. The non-detachable internal cannula 26 is sealed with the scalpel bar 27 by a far-end sealing ring 263, and the far-end sealing ring 263 may be fixedly connected to the scalpel bar 27 in a form of encapsulating and curing and also may be fixedly connected to the internal cannula 261. Optimally, a shaft shoulder 271 is provided the outer surface of the scalpel bar 27, a full-circle groove structure 2631 is provided on the inner surface of the far-end sealing ring 263, and the shaft shoulder 271 is in tight fit with the full-circle groove structure 2631. Sealing of the non-detachable internal cannula 26 with the detachable cannula component 25 is achieved by a near-end sealing ring 264, specifically, the internal cannula fastener 262 is provided at the near end of the non-detachable internal cannula 26, a rolling slot 2621 is provided on the internal cannula fastener 262, and the near-end sealing ring 264 is also located in the rolling slot 2621, so that the near-end sealing ring 264 rolls in clearances of the external cannula fastener 254 and the internal cannula fastener 262 when implementing the closing and opening functions of the clamp forceps 251, so as to avoid damage of the near-end sealing ring 264 due to sliding wear.

According to an implementation mode of the present application, a function of mounting or dismounting between an instrument body 24 and a detachable cannula component 25 is implemented by a first detachable structure 41 and a second detachable structure 42. The first detachable structure 41 is as shown in FIG. 17 to FIG. 20, is a fixed connection structure between the instrument body 24 and the cannula component 25, and can fixedly connect the instrument body 24 with the cannula component 25; the second detachable structure 42 is as shown in FIG. 21 to FIG. 24, is a drive connection structure of the instrument body 24 and the cannula component 25, and can realize drive control of the instrument body 24 on the clamp forceps 251 of the cannula component 25. The second detachable structure 42 is coaxial with the first detachable structure 41 and can implement definite movement relative to the first detachable structure 41 along the axial direction of the scalpel bar.

Referring to FIGS. 17-20, in the ultrasonic surgical instrument with a detachable cannula according to the second embodiment of the present application, the first detachable structure 41 includes a first boss 412 at a near end of a detachable cannula component 25, and a T-shaped limiting slot 411, a stopper 413 and an elastic element 414 located on the instrument body. A person killed in the art may easily think that positions of the first boss and the T-shaped limiting slot 411 as well as the stopper 413 are interchangeable, that is, the first boss is provided on the instrument body 4, while the T-shaped limiting slot 411, the stopper 413 and the elastic element 28 are provided on the detachable cannula component 25.

Figure 17:
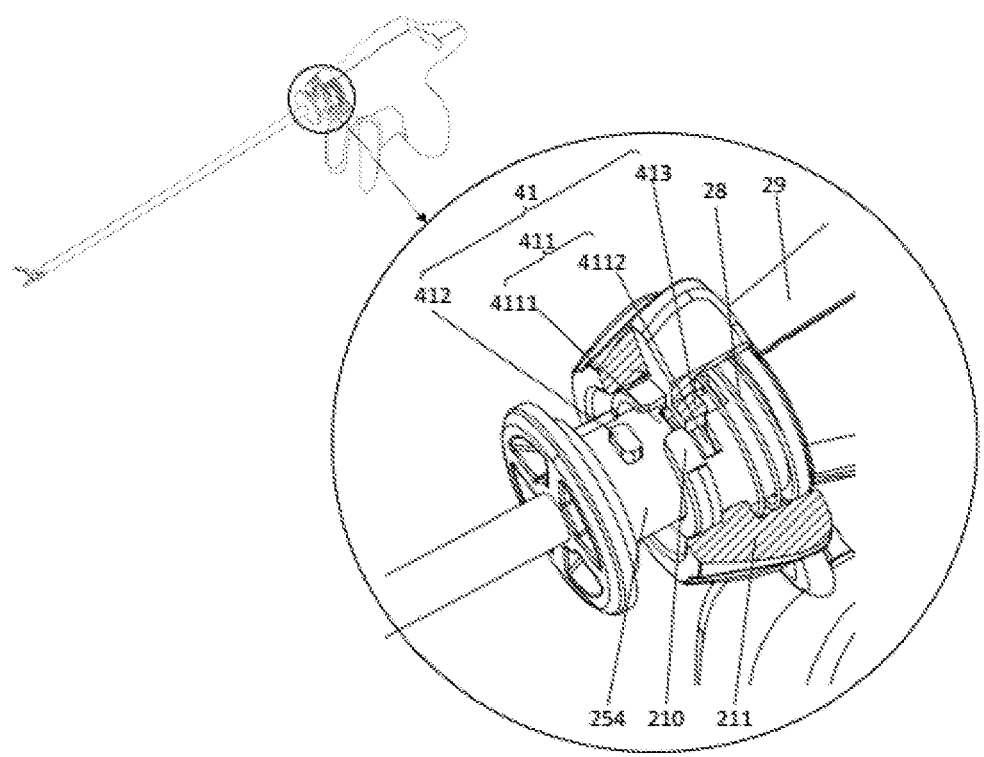
FIG. 17 is a schematic diagram of a first detachable structure in FIG. 14: wherein the first boss is about to enter the T-shaped limiting slot.

Specifically, a fixed seat 210 is provided on a shell 241 of the instrument body 24, the T-shaped limiting slot 411 is provided on the fixed seat 210, and the T-shaped limiting slot 411 includes a transverse slot parallel to the longitudinal axis of the scalpel bar and a vertical slot 4112 vertical to the longitudinal axis of the scalpel bar; the first boss 412 is provided on the external cannula fastener 254. The first boss 412 is capable of sliding along the axis direction of the scalpel bar in the transverse slot 4111 of the T-shaped limiting slot, and also is capable of sliding by being vertical to the axis direction of the scalpel bar in the vertical slot 4112 of the T-shaped limiting slot; the stopper 413 is capable of sliding along the axis direction of the scalpel bar in the transverse slot 4111 of the T-shaped limiting slot, while incapable of entering the vertical slot 4112 of the T-shaped limiting slot. The stopper 413 is connected with the elastic element 28, the elastic element 28 can provide an elastic force along the direction of the transverse slot 4111 of the T-shaped limiting slot, and the stopper is located at an intersected point of the transverse slot and the vertical slot of the T-shaped limiting slot in an initial state under the action of the elastic force of the elastic element 8. Refer to FIG. 17, a fixed seat 210 is provided on a shell 241 of the instrument body 24, a thumbwheel 211 is mounted on the fixed seat 210, the T-shaped limiting slot 411 is provided on the fixed seat 210, and the stopper 413 is provided on the thumbwheel 211.

Figure 18:
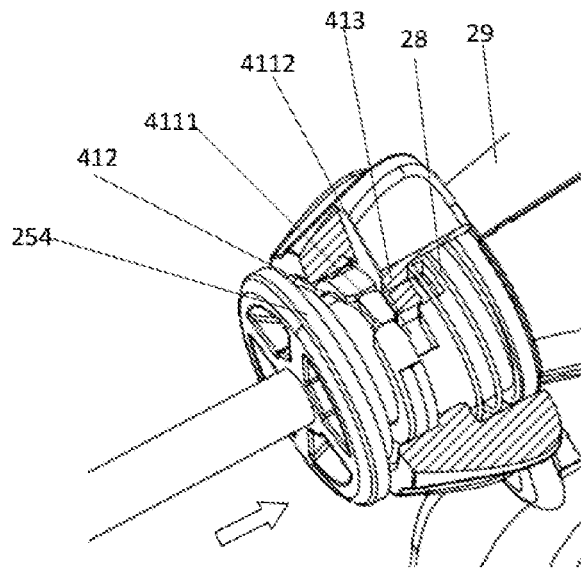
FIG. 18 is a schematic diagram of a first detachable structure in FIG. 14: a schematic diagram that the first boss enters an intersection of the T-shaped limiting axial slot and an axial slot.
Figure 19:
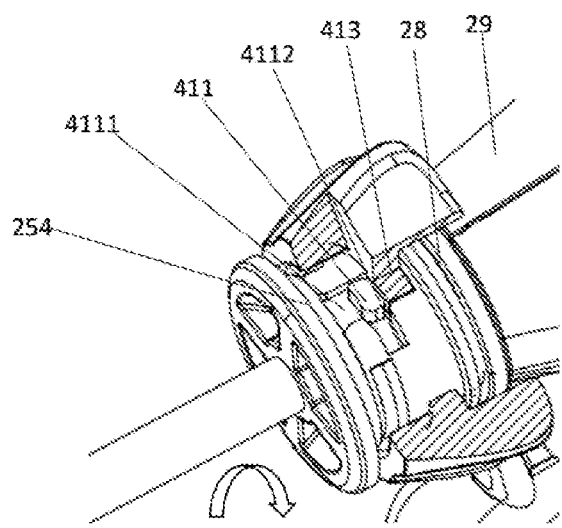
FIG. 19 is a schematic diagram of a first detachable structure in FIG. 14: a schematic diagram that the first boss enters a half position of the axial slot of the T-shaped limiting slot.
Figure 20:
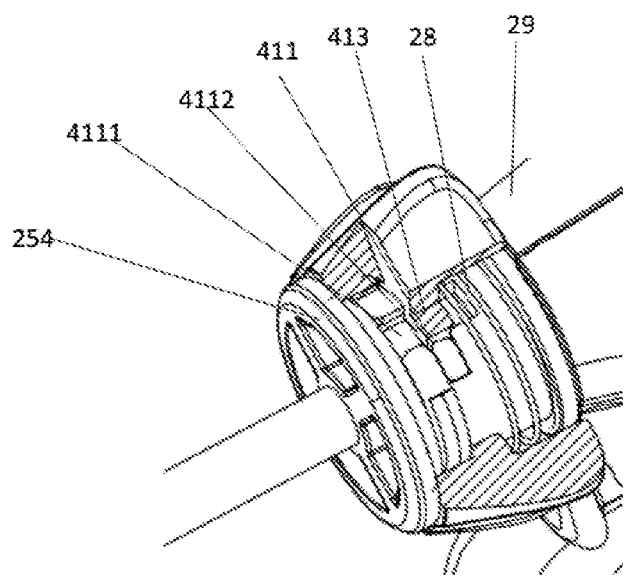
FIG. 20 is a schematic diagram of a first detachable structure in FIG. 14: a schematic diagram that the first boss enters the axial slot of the T-shaped limiting slot and is blocked by the stopper.

Referring to FIGS. 17-20, wherein FIG. 17 shows that a first boss 412 is about to enter a T-shaped limiting slot 411. In an initial state, under the action of the elastic force of an elastic element 28, the stopper 413 is located at an intersected point of a transverse slot 4111 and a vertical slot 4112 of the T-shaped limiting slot to seal an outlet of the vertical slot 4112. When the first boss 412 continues to slide towards the inside of the transverse slot 4111 of the T-shaped limiting slot 411 under the action of an external force, the stopper 413 needs to be pushed to slide in the transverse slot 4111 by overcoming the elastic force of the elastic element 28. FIG. 18 shows a situation when the first boss 412 enters an intersection of the transverse slot 4111 and the vertical slot 4112, at the moment, by rotating the external cannula fastener 254, the first boss 412 can be driven to slide into the vertical slot 4112 of the T-shaped limiting slot, and FIG. 19 shows such state. Continuing to rotate the external cannula fastener 254, causes the first boss 412 to completely slide into the vertical slot 4112, and the stopper 413 returns to the intersection of the transverse slot 4111 and the vertical slot 4112 under the action of the elastic element 8, so as to seal an outlet of the vertical slot 4112 to completely confine the first boss 412 in the vertical slot 4112, FIG. 20 describes such state, at the moment, the external cannula fastener 254 is fixed on the fixed seat 210, and fixed connection between the cannula component 25 and the instrument body 24 is completed by a first detachable structure 41.

When the cannula component 25 is dismounted from the instrument body 24, it is basically a reverse operation of the process described in FIG. 17 to FIG. 20. Firstly, a thumbwheel 211 is pulled towards a near end along the axis direction of the scalpel bar by overcoming the elastic force of the elastic element 28, so that the stopper 413 opens an intersection of the transverse slot 4111 and the vertical slot 4112 of the T-shaped limiting slot 411, then the external cannula fastener 254 is rotated to cause the first boss 412 to slide into the transverse slot 4111 from the vertical slot 4112 of the T-shaped limiting slot 411, and then the cannula component 25 is pulled out from the instrument body 24 along the axis direction of the scalpel bar to cause the first boss 412 to slide out of the transverse slot 4111, thus completing the dismounting process. In such process, along with the movement of the first boss 412 towards a far side along the transverse slot from the intersection of the transverse slot 4111 and the vertical slot 4112, the stopper 413 returns to the intersection of the transverse slot 4111 and the vertical slot 4112 under the action of elastic force of the elastic element 28.

A person of ordinary skill in the art may understand that multiple first detachable structures 41 may be provided by taking the scalpel bar 27 as an axis, and specific implementation modes thereof all fall within the protection scope of the present application.

Referring to FIG. 21-24, in the ultrasonic surgical instrument with a detachable cannula component according to the second embodiment of the present application, the second detachable structure 42 includes an L-shaped limiting slot 421 located on a detachable internal cannula 253 and a second boss 422 located on a non-detachable internal cannula 262 of the instrument body. A person skilled in the art may easily think that positions of the second boss and the L-shaped limiting slot are interchangeable.

Figure 21:
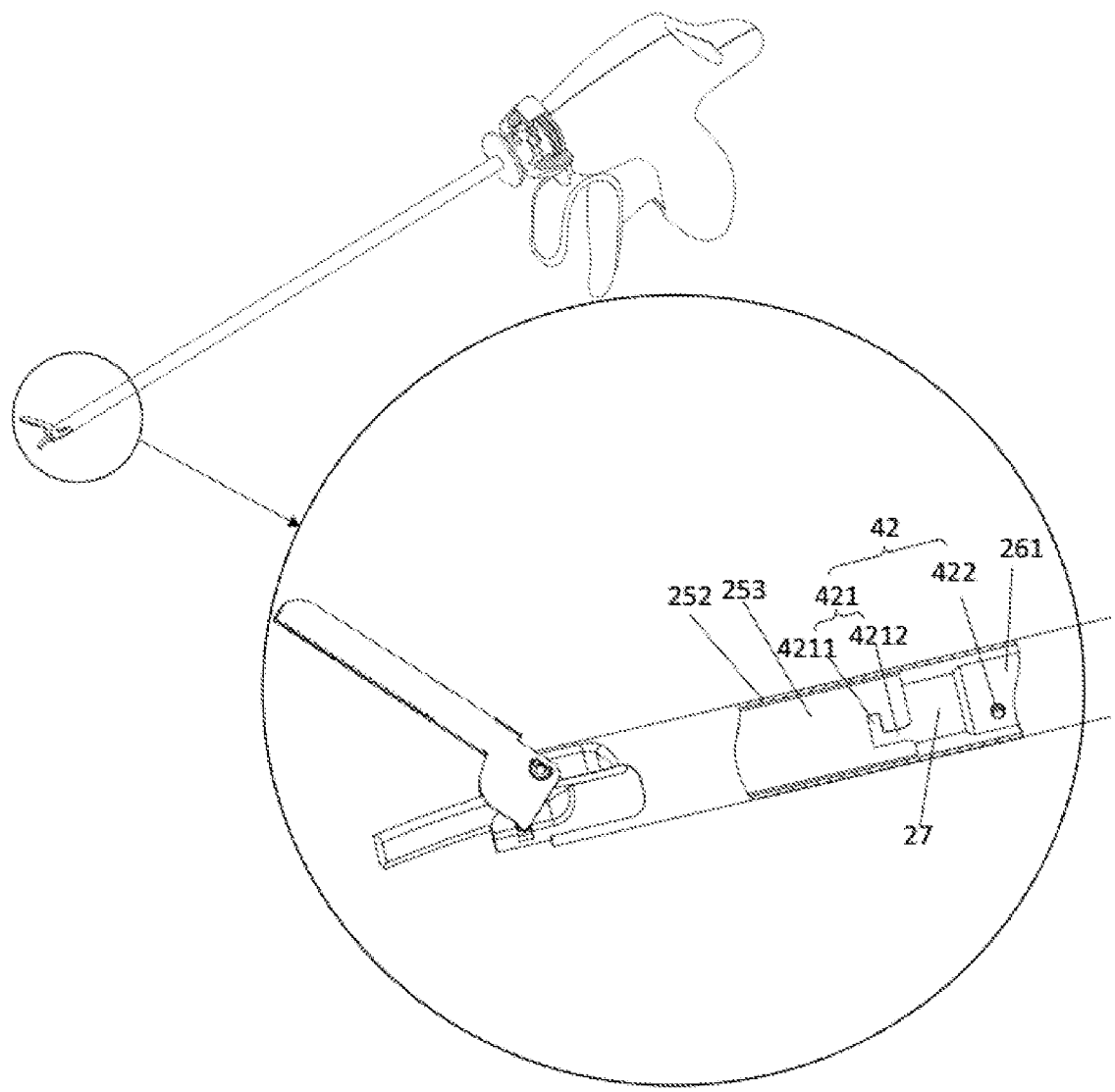
FIG. 21 is a schematic diagram of a second detachable structure in FIG. 14: a schematic diagram that the second boss does not enter the L-shaped limiting slot.

FIG. 21 shows a detailed schematic structure diagram of the L-shaped limiting slot 421 and the second boss 422, and an L-shaped limiting slot structure 421 and a second boss 422 are shown in FIG. 21. In another implementation mode, two or multiple L-shaped limiting slot structures 421 are provided on the detachable internal cannula 253, correspondingly, two or multiple second bosses 422 are provided on the non-detachable internal cannula 261 of the instrument body 24.

Figure 22:
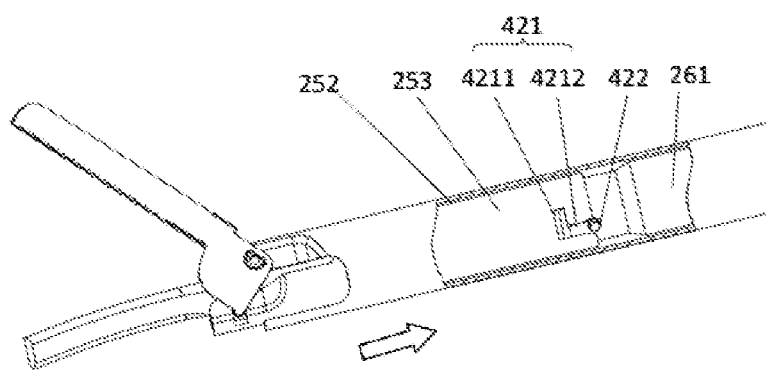
FIG. 22 is a schematic diagram of a second detachable structure in FIG. 14: a schematic structure diagram that the second boss enters the L-shaped limiting slot.
Figure 23:
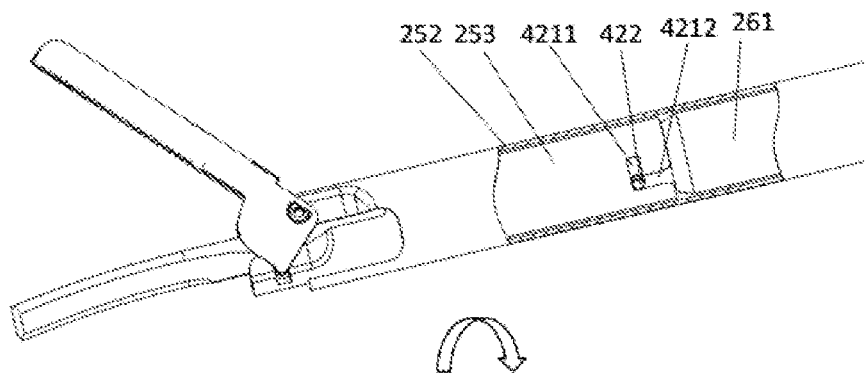
FIG. 23 a schematic diagram of a second detachable structure in FIG. 14: a schematic structure diagram that the second boss enters the axial slot of the L-shaped limiting slot.
Figure 24:
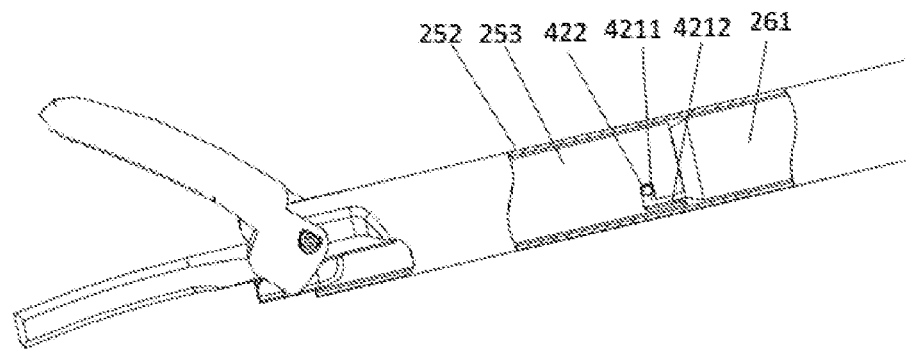
FIG. 24 is a schematic diagram of a second detachable structure in FIG. 14: a schematic diagram that the second boss enters the axial slot of the L-shaped limiting slot.

FIGS. 22, 23, 24 show a mounting process of a second detachable structure 42, and under the effects of stop and push of the first detachable structure 41, the second detachable structure 42 moves along with the movement of the first detachable structure 41 in the process of mounting or dismounting the cannula component 25 and the instrument body 24. Specifically, as shown in FIG. 22, when the first boss 412 on the first detachable structure 41 is about to enter the T-shaped limiting slot 411, the second boss 422 on the second detachable structure 42 also is about to enter the L-shaped limiting slot 421. As shown in FIG. 23, when the first boss 412 on the first detachable structure 41 completely enters the transverse slot 4111 the T-shaped limiting slot 411, the second boss 422 on the second detachable structure 42 also completely enters the transverse slot of the L-shaped limiting slot 421. As shown in FIG. 24, when the external cannula fastener 254 is rotated to cause the first boss 412 on the first detachable structure 41 to completely enter the vertical slot 4112 of the T-shaped limiting slot 411, the detachable internal cannula 253 rotates therewith, so that the second boss 422 on the second detachable structure 42 also completely enters the vertical slot 4211 of the L-shaped limiting slot 421. At the moment, the non-detachable internal cannula 261 and the detachable internal cannula 253 complete drive connection, to realize drive control of the instrument body 24 on the cannula component 25. When the cannula component 25 is dismounted from the instrument body 24, it is a reverse process of the foregoing process, and is not further described herein.

A person of ordinary skill in the art may understand that one or multiple second detachable structures 42 may be provided, optimally, the multiple second detachable structures 42 are symmetrically arranged by taking the scalpel bar 27 as axis, and specific implementation modes all fall within the protection scope of the present application.

It should to be noted that implementation schemes in the accompanying drawings are merely representative embodiments of the present application, a person skilled in the art may easily understand that the protection scope of the present application is not merely limited in a scope defined by implementation modes in the accompanying drawings, and combination, transformation and variation for implementation modes in the drawings all fall within the protection scope of the present application.

The ultrasonic surgical instrument with a detachable cannula component according to the present application solves the problems that mainstream ultrasonic surgical instruments on the market are difficult to clean after use, and cannot be repeatedly used, and can remarkably lower the use cost of the instrument. Moreover, in comparison with technical schemes in the prior art, reusable parts in the ultrasonic surgical instrument with a detachable cannula component of the present application are increased, so as to further lower the use cost, moreover, convenience in mounting and dismounting, reliability of the overall structure, and simplicity in implementation of the process are all promoted. In brief, the present application has the advantages of being simple in stricture, convenient in mounting and dismounting and low in cost in comparison with the prior art.

The foregoing disclosed are merely several preferred embodiments of the present application, of course, the protection scope of the present application should be not limited hereby, therefore, equivalent variations made according to claims of the present application still belong to a coverage scope of the present application.

What is claimed is:

1. An ultrasonic surgical instrument comprising:
a cannula component; and
an instrument body, wherein the instrument body includes a scalpel bar for realizing an ultrasonic cutting effect, and wherein the cannula component is detachably connected to the instrument body by a detachable structure along a longitudinal axis of the scalpel bar, wherein
the detachable structure comprises at least one first detachable component, and the instrument body is connected with the cannula component by the at least one first detachable component,
the at least one first detachable component comprises a first boss, a first limiting slot, and a stopper,
the first boss is located on the cannula component, and the first limiting slot and the stopper are located on the instrument body; or the first boss is located on the instrument body, and the first limiting slot and the stopper are located on the cannula component,
the first limiting slot comprises a first slot parallel to the longitudinal axis of the scalpel bar and a second slot circumferential to the longitudinal axis of the scalpel bar,
the first boss is configured to slide along the direction of the longitudinal axis of the scalpel bar in the first slot of the first limiting slot, and slide rotationally about the longitudinal axis of the scalpel bar in the second slot of the first limiting slot,
the stopper is configured to slide along the direction of the longitudinal axis of the scalpel bar in the first slot of the first limiting slot, while being incapable of entering the second slot of the first limiting slot, and
the detachable structure comprises a second detachable component, and the second detachable component comprises a second limiting slot located on the cannula component and a second boss located on the instrument body.

2. The ultrasonic surgical instrument according to claim 1, wherein the at least one first detachable component comprises an elastic element.

3. The ultrasonic surgical instrument according to claim 2, wherein,
if the first boss is located on the instrument body, the elastic element is located on the cannula component, or
if the first boss is located on the cannula component, the elastic element is located on the instrument body.

4. The ultrasonic surgical instrument according to claim 2, wherein
the stopper is connected with the elastic element, the elastic element being configured to provide an elastic force along the direction of the first slot, and wherein the stopper is located at an intersection point of the first slot and the second slot of the first limiting slot in an initial state under the action of the elastic force of the elastic element.

5. The ultrasonic surgical instrument according claim 4, wherein the cannula component comprises an internal cannula, an external cannula, and a clamp arm and a blade located at a far end of the surgical instrument,
wherein the external cannula and the internal cannula are coaxial with respect to the scalpel bar and the clamp arm is rotatably connected with the external cannula by a first rotating shaft and rotatably connected with the internal cannula by a second rotating shaft, so that the internal cannula is pulled forwards and backwards along an axial direction to drive the clamp arm to rotate around the first rotating shaft.

6. The ultrasonic surgical instrument according to claim 5, wherein the instrument body is in drive connection with the internal cannula via the second detachable component.

7. The ultrasonic surgical instrument according to claim 6, wherein the second detachable component moves along with a movement of the at least one first detachable component while mounting or dismounting the cannula component with respect to the instrument body,
wherein the first boss on the at least one first detachable component enters the first limiting slot, and the second boss on the second detachable component enters the second limiting slot simultaneously;
wherein the first boss on the at least one first detachable component enters the intersection point of the first slot and the second slot of the first limiting slot, and the second boss on the second detachable component enters a second intersection point of a first slot and a second slot of the second limiting slot simultaneously, and wherein
when the external cannula is rotated to cause the first boss on the at least one first detachable component to completely enter the second slot from the first slot of the first limiting slot, the internal cannula rotates therewith, so that the second boss on the second detachable component completely enters the second slot from the first slot of the second limiting slot.

8. The ultrasonic surgical instrument according to claim 7, wherein the second limiting slot is located in the internal cannula, and the second boss is located on the instrument body.

9. The ultrasonic surgical instrument according to claim 8, wherein the first slot of the second limiting slot is along the direction of the longitudinal axis of the scalpel bar, and the second slot of the second limiting slot is circumferential to the direction of the longitudinal axis of the scalpel bar and wherein, the second boss is configured to slide along the direction of the longitudinal axis of the scalpel bar in the first slot of the second limiting slot and slide rotationally about the longitudinal axis of the scalpel bar in the second slot of the second limiting slot.

10. The ultrasonic surgical instrument according to claim 9, wherein the cannula component further comprises an external cannula fastener and an internal cannula fastener, the external cannula fastener being connected with the external cannula, and the internal cannula fastener being connected with the internal cannula.

11. The ultrasonic surgical instrument according to claim 10, wherein the first boss is provided on the external cannula fastener, and the second limiting slot is provided on the internal cannula fastener.

12. The ultrasonic surgical instrument according to claim 11, wherein
a fixed seat is provided on the instrument body,
the first limiting slot is provided on the fixed seat,
a thumbwheel and the elastic element are mounted on the fixed seat,
the stopper is provided on the thumbwheel, and wherein the thumbwheel is configured to drive the stopper along the direction of the first slot of the first limiting slot by overcoming the elastic force of the elastic element so that the stopper opens the intersection point of the first slot and the second slot of the first limiting slot.

13. The ultrasonic surgical instrument according to claim 12, wherein a driving seat is connected to the instrument body, the second boss is provided on the driving seat, the driving seat and the second boss are configured to move in a direction along the axis of the scalpel bar by a manual control mechanism on the instrument body.

14. The ultrasonic surgical instrument according to claim 2, wherein the first boss is located on the instrument body, and the first limiting slot, the stopper, and the elastic element are located on the cannula component.

15. The ultrasonic surgical instrument according to claim 14,
wherein the stopper is connected with the elastic element, the elastic element being configured to provide an elastic force along the direction of the first slot, and wherein the stopper is located at an intersection point of the first slot and the second slot of the first limiting slot in an initial state under the action of the elastic force of the elastic element.

16. An ultrasonic surgical instrument comprising:
a cannula component; and
an instrument body, wherein the instrument body includes a scalpel bar for realizing an ultrasonic cutting effect, and wherein the cannula component is detachably connected to the instrument body by a detachable structure along a longitudinal axis of the scalpel bar, wherein
the detachable structure comprises at least one first detachable component, and the instrument body is connected with the cannula component by the at least one first detachable component,
the at least one first detachable component comprises a first boss, a first limiting slot, and a stopper,
the first boss is located on the cannula component, and the first limiting slot and the stopper are located on the instrument body; or the first boss is located on the instrument body, and the first limiting slot and the stopper are located on the cannula component,
the first limiting slot comprises a first slot circumferential to the longitudinal axis of the scalpel bar and a second slot parallel to the longitudinal axis of the scalpel bar,
the first boss is configured to slide along the direction of the longitudinal axis of the scalpel bar in the second slot of the first limiting slot, and slide rotationally about the longitudinal axis of the scalpel bar in the first slot of the first limiting slot, and
the stopper is configured to slide by being vertical to the direction of the longitudinal axis of the scalpel bar in the first slot of the first limiting slot, while being incapable of entering the second slot of the first limiting slot.

* * * * *